United States Patent
Russell et al.

(10) Patent No.: US 9,775,561 B2
(45) Date of Patent: Oct. 3, 2017

(54) SYSTEM METHOD AND DEVICE FOR MONITORING PHYSIOLOGICAL PARAMETERS OF A PERSON

(75) Inventors: Brian K. Russell, Crownsville, CT (US); Jonathan Woodward, Annapolis, MD (US); William Radtke, Ellicott City, MD (US); Christopher Dykes, Columbia, MD (US)

(73) Assignee: Covidien LP, Mansfield, MA (US)

( * ) Notice: Subject to any disclaimer, the term of this patent is extended or adjusted under 35 U.S.C. 154(b) by 750 days.

(21) Appl. No.: 13/331,544

(22) Filed: Dec. 20, 2011

(65) Prior Publication Data
US 2012/0165645 A1    Jun. 28, 2012

Related U.S. Application Data

(60) Provisional application No. 61/426,836, filed on Dec. 23, 2010.

(51) Int. Cl.
| A61B 5/0408 | (2006.01) |
| A61B 5/00 | (2006.01) |
| A61B 5/024 | (2006.01) |
| A61B 5/08 | (2006.01) |
| A61B 5/11 | (2006.01) |

(52) U.S. Cl.
CPC .......... *A61B 5/6804* (2013.01); *A61B 5/0024* (2013.01); *A61B 5/6823* (2013.01); *A61B 5/024* (2013.01); *A61B 5/0408* (2013.01); *A61B 5/0816* (2013.01); *A61B 5/1116* (2013.01); *A61B 5/1118* (2013.01); *A61B 2562/16* (2013.01); *A61B 2562/227* (2013.01)

(58) Field of Classification Search
CPC ....... A61B 5/04; A61B 5/0402; A61B 5/0416; A61B 5/0478; A61B 5/6802; A61B 5/6804–5/6806; A61B 5/6814; A61B 5/6823; A61B 5/6831; A61B 2562/16; A61B 5/0408
USPC ....... 600/372, 386, 509, 382, 388–390, 383; 439/909, 37, 153, 261, 282, 310, 439/312–321, 550, 569; 174/559–564
See application file for complete search history.

(56) References Cited

U.S. PATENT DOCUMENTS

| 4,889,131 | A | * | 12/1989 | Salem | A61B 5/0006 128/903 |
| 5,657,201 | A | * | 8/1997 | Kochis | 361/679.41 |
| 6,895,261 | B1 | * | 5/2005 | Palamides | H04B 1/385 455/100 |
| D603,521 | S | * | 11/2009 | Lindberg et al. | D24/187 |
| 8,083,693 | B1 | * | 12/2011 | McKeon | A61B 5/103 600/587 |
| 8,909,318 | B2 | * | 12/2014 | Nordstrom | A61B 5/0006 600/388 |
| 9,119,594 | B2 | * | 9/2015 | Oleson | A61B 5/6804 |
| 2001/0044573 | A1 | * | 11/2001 | Manoli et al. | 600/383 |
| 2002/0124295 | A1 | * | 9/2002 | Fenwick | A41D 13/1245 2/69 |
| 2002/0128686 | A1 | * | 9/2002 | Minogue et al. | 607/2 |

(Continued)

FOREIGN PATENT DOCUMENTS

WO    WO 2009112976 A1 *  9/2009    ............... A61B 5/00

*Primary Examiner* — Lee S Cohen
*Assistant Examiner* — Erin M Cardinal (57) ABSTRACT

Provided is a system, method and portable device for monitoring physiological parameters of a person in the field.

6 Claims, 12 Drawing Sheets

(56) References Cited

U.S. PATENT DOCUMENTS

| | | | | |
|---|---|---|---|---|
| 2007/0088419 A1* | 4/2007 | Fiorina | ............... | A61N 1/0476 607/152 |
| 2007/0089800 A1* | 4/2007 | Sharma | ........................ | 139/388 |
| 2007/0279852 A1* | 12/2007 | Daniel et al. | ................. | 361/683 |
| 2007/0285868 A1* | 12/2007 | Lindberg | ............. | A61B 5/0245 600/382 |
| 2008/0108890 A1* | 5/2008 | Teng | ................. | A61B 5/04087 600/372 |
| 2008/0288026 A1* | 11/2008 | Cross | ................. | A61B 5/0408 607/60 |
| 2010/0185398 A1* | 7/2010 | Berns et al. | .................... | 702/19 |
| 2012/0078127 A1* | 3/2012 | McDonald | .............. | A61B 5/11 600/508 |
| 2012/0101396 A1* | 4/2012 | Solosko et al. | ............... | 600/509 |
| 2012/0246795 A1* | 10/2012 | Scheffler et al. | ................... | 2/69 |
| 2012/0330126 A1* | 12/2012 | Hoppe et al. | ................. | 600/391 |
| 2013/0019383 A1* | 1/2013 | Korkala | .............. | A61B 5/6804 2/338 |

* cited by examiner

SYSTEM METHOD AND DEVICE FOR MONITORING PHYSIOLOGICAL PARAMETERS OF A PERSON

CROSS-REFERENCE TO RELATED APPLICATIONS

This application claims priority to U.S. Provisional Patent Application Ser. No. 61/426,836, filed 23 Dec. 2010, the complete disclosure of which is incorporated herein by reference.

BACKGROUND OF THE INVENTION

The present invention generally relates to physiological data processing and more particularly, to a system, method and portable device for monitoring physiological parameters of a person in the field.

A person's physiological parameters are traditionally monitored in clinical setting. However, field based monitoring has advantages of being able to monitor the physiological parameters over an extended period of time (e.g., hours or days versus minutes), in a person's typical environment, and during activities of that person. For example, it may be desirable to monitor the vital signals of an athlete (e.g., a professional, collegiate, or high school football, basketball, or baseball player) during a game or during practice for a game and in the athlete's environment (e.g., on the (hot or cold) football field, basketball court, etc.). Similarly, it may be desirable to monitor a patient's vital signs over an extended period of time in the patient's home and/or work place. In addition, monitoring vital signs over extended time periods (in the field) provides more useful information to allow an understanding of a person's physiological state.

It may be desirable for a biosensor sensor system that includes one or more sensors that are integrated or attached to the garment and wherein the biosensor monitoring device is removably attached to the garment.

There are various challenges to removably attaching a monitoring device to a garment. Specifically, the monitoring device must be easily connected to the garment by the user, but in a secure manner so that it does not inadvertently get dislodged. Second, the connections system must satisfy various manufacturability, performance, and usability requirements. Third, it is desirable to reduce or minimize the interference caused by the monitoring device with the user's activities.

These and other advantages may be provided by one or more embodiments of the present invention.

SUMMARY OF THE INVENTION

The above objectives and other objectives are obtained by a device for attaching an electronics portion to a garment, comprising:
 a housing enclosing at least a portion of the electronics portion;
 an interface configured to be fixedly attached to the garment;
 said housing having a plurality of housing sensor pads;
 said housing configured to be removably attached to said interface; and
 said interface having a plurality of sensor pads positioned to contact the plurality of housing sensor pads when said housing is attached to said interface.

DETAILED DESCRIPTION OF ILLUSTRATIVE EMBODIMENTS

In the following description, for purposes of explanation and not limitation, specific details are set forth, such as particular networks, communication systems, computers, terminals, devices, components, techniques, data and network protocols, software products and systems, operating systems, development interfaces, hardware, etc. in order to provide a thorough understanding of the present invention.

However, it will be apparent to one skilled in the art that the present invention may be practiced in other embodiments that depart from these specific details. Detailed descriptions of well-known networks, communication systems, computers, terminals, devices, components, techniques, data and network protocols, software products and systems, operating systems, development interfaces, and hardware are omitted so as not to obscure the description.

The present invention provides a system, device and method of connecting a monitoring device of a biosensor system to a garment and where one or more sensors are attached or integrated into the garment.

Figure 1:
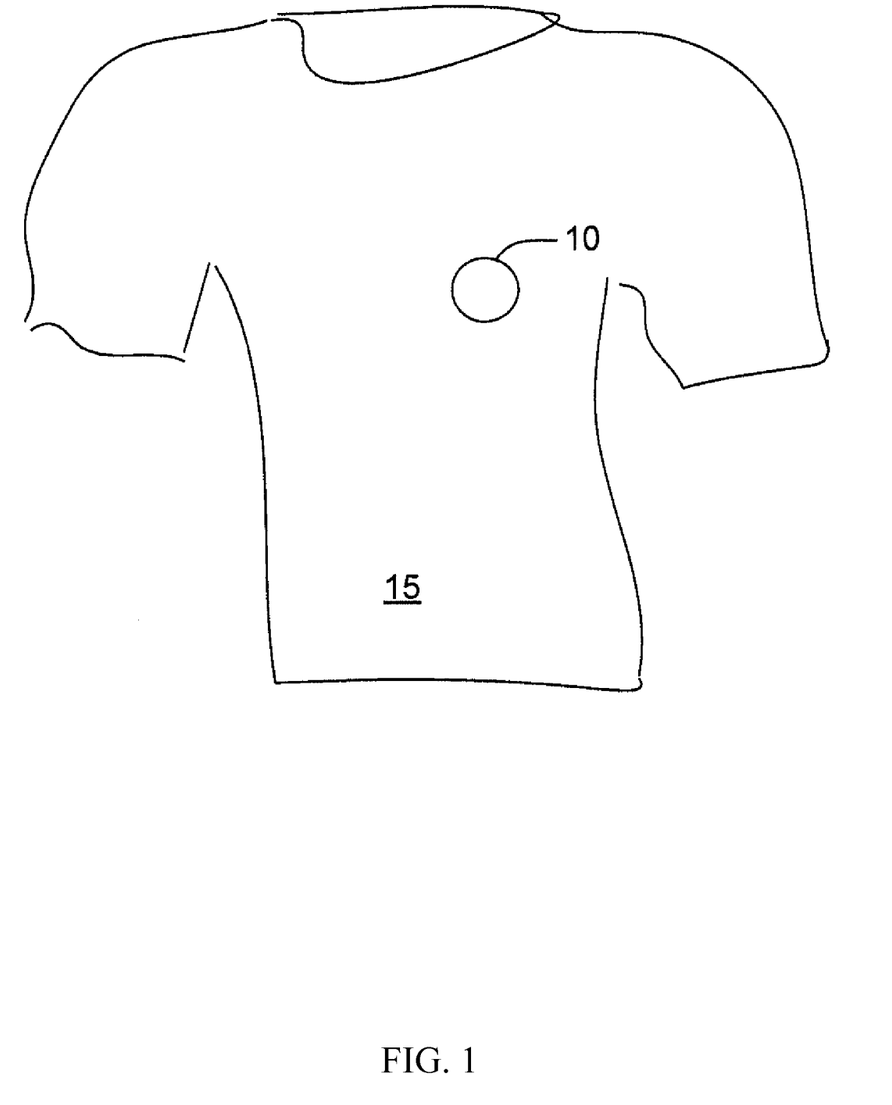
FIG. 1 illustrates a monitoring device attached to a garment.
Figure 2:
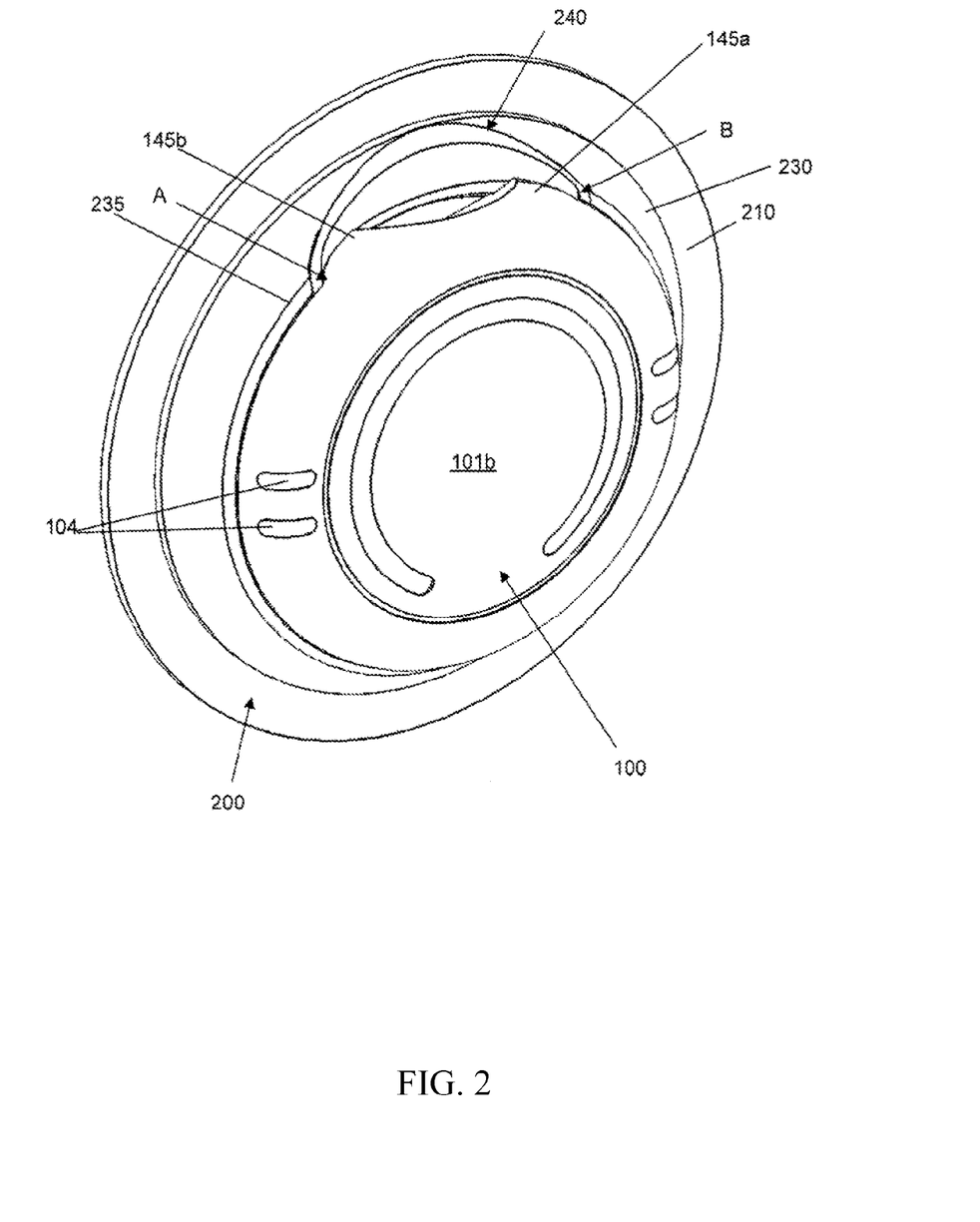
FIG. 2 illustrates a monitoring device.
Figure 3:
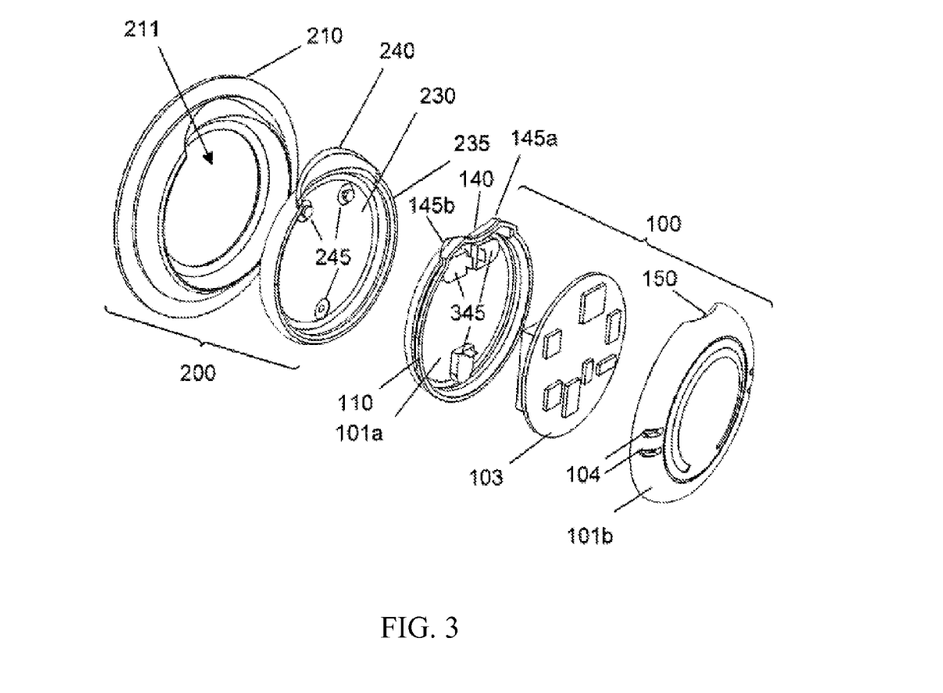
FIG. 3 illustrates a monitoring device.

Example embodiments of the present invention may be used to connect a monitoring device to sensors that are attached to or integrated into a garment and have that has the functionality of the BioHarness®, which is commercially available and manufactured by Zephyr Technology of Annapolis, Md. As illustrated in FIG. 1, the monitoring device 10 is attached to the garment 15 (a shirt) in the chest area. In other embodiments, the monitoring device may be connected to the garment on the upper arm or on the side (under the arm). Example embodiments of the monitoring device 10 may measure heart rate, breathing rate, temperature, activity and/or posture. The monitoring device 10 may include a battery and have a Bluetooth wireless transceiver (and/or one or more other transceivers such as ZigBee (IEEE 8902.154 under Zigbee), ANT, etc.), a processor, and internal memory. Where multiple transceivers are included, two, three or more transceivers may be operational (and operate) concurrently to allow simultaneous communications with different remote devices. The person may wear the device at home and/or work (or in a clinic environment). The data from the biomechanical and physiological sensors (and in some embodiments environmental sensors that measure ambient temperature, humidity, altitude, etc.) is regularly collected and stored in memory. Processing of collected data may be performed by an algorithm executed on the monitoring device 10 or a computer that receives the data from the collection device.

FIGS. 2-5 illustrate a monitoring device 100 and interface 200 according to an example embodiment of the present invention. The monitoring device 100 comprises a bottom portion 101a and top portion 101b that mate together to house an internal portion 103 that comprises a processor, electronics, one or more transceivers, one or more light emitting LEDs (that are arranged to be visible through apertures 104 in the top portion 101b). The bottom portion 101a may include leaf springs 345 (or other sensor pads) that conduct data from a plurality of sensors in or attached to the garment to the electronics (e.g., an ADC, DSP, or processor) of the internal portion 103.

The interface 200 comprises a receptacle portion 230 that is fixedly attached to mounting member 210. In this example, member 210 comprises an elastomeric ring having an aperture 211 therethrough. Receptacle portion 230 includes rim 235 that extends around the perimeter of the receptacle portion except for a lip portion 240. In addition, receptacle portion 230 includes three sensor pads 245, which may comprise rivets that extend through the garment. Each sensor pad is electrically connected to one or more sensors attached to or integrated into the garment 15. In this example, one of the sensor pads connects to a sensor ground, one connects to an ECG sensor, and one sensor pad connects to a breathing rate sensor. Member 210 is fixedly attached to the garment 15 such as by being heat bonded or sewn on, although other methods may be used. Thus, the sensor pads 245 may be connected to sensors in the garment via rivets (or conductors) that extend through the aperture 211 of the member 210 to other locations on the garment (which may be outside the circumference of the ring).

Bottom portion 101a includes an indentation 140 and similarly top portion 101b includes an indentation 150. When top portion 101b and bottom portion 101a are mated together the indentation in the monitoring device 100 is designed to align with the lip 240 in the receptacle portion 230 of the interface 200. To ensure that alignment, some embodiments of the invention may include a key system. Specifically, in this embodiment the bottom portion 101a includes a first protrusion 145a and a second protrusion 145b that protrude slightly downward and radially outward (further than the rim 110 of bottom portion 101a). Each protrusion 145 is positioned to protrude into the space adjacent the lip portion 240 and to abut against the rim portion 235 at points A and B.

The assembled monitoring device 100 is designed to "snap" into the receptacle portion of the interface 200. The protrusions 145a-b ensure that the monitoring portion 100 is correctly oriented with respect to the interface 200 to ensure that leaf springs 345 of the monitoring device 100 align with and contact the sensor pads 245 (which may comprise rivets that protrude from the garment through member 210) of the receptacle portion 230 when inserted.

Figure 4:
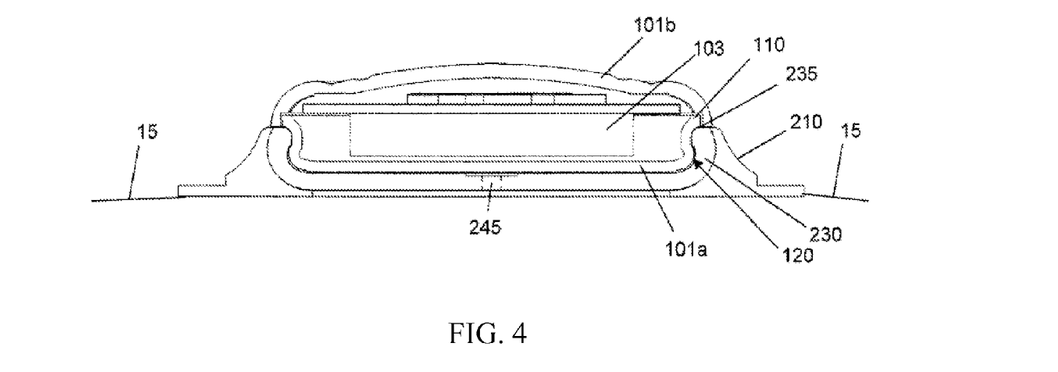
FIG. 4 illustrates a monitoring device.
Figure 5:
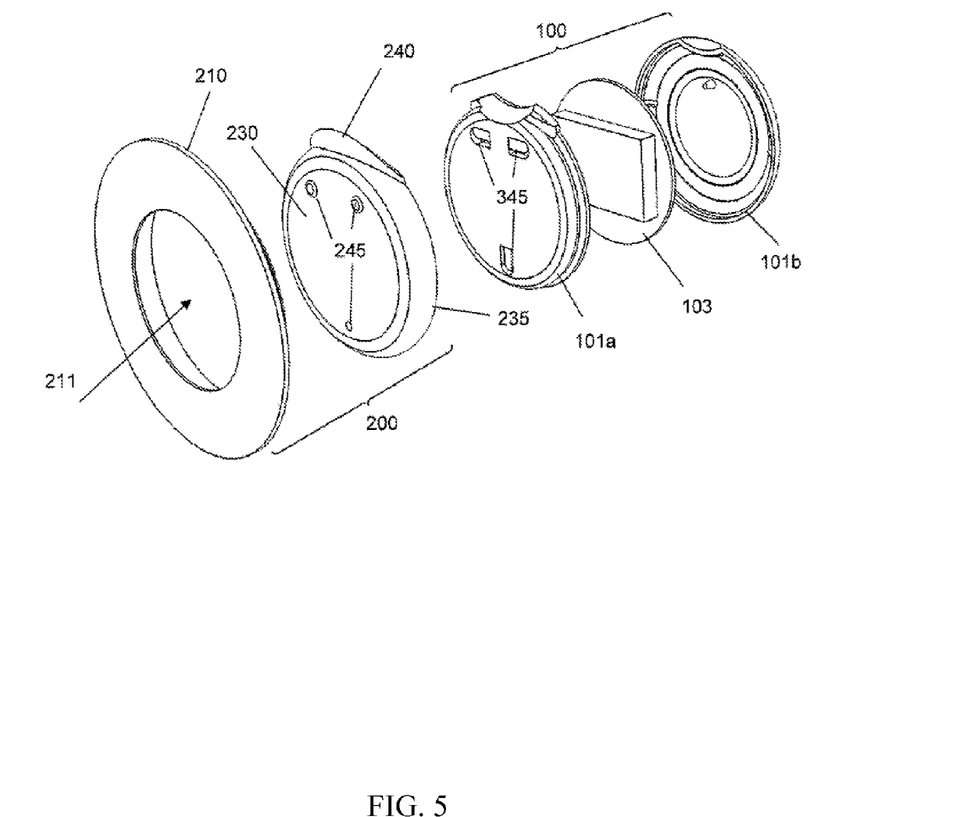
FIG. 5 illustrates a monitoring device.
Figure 6:
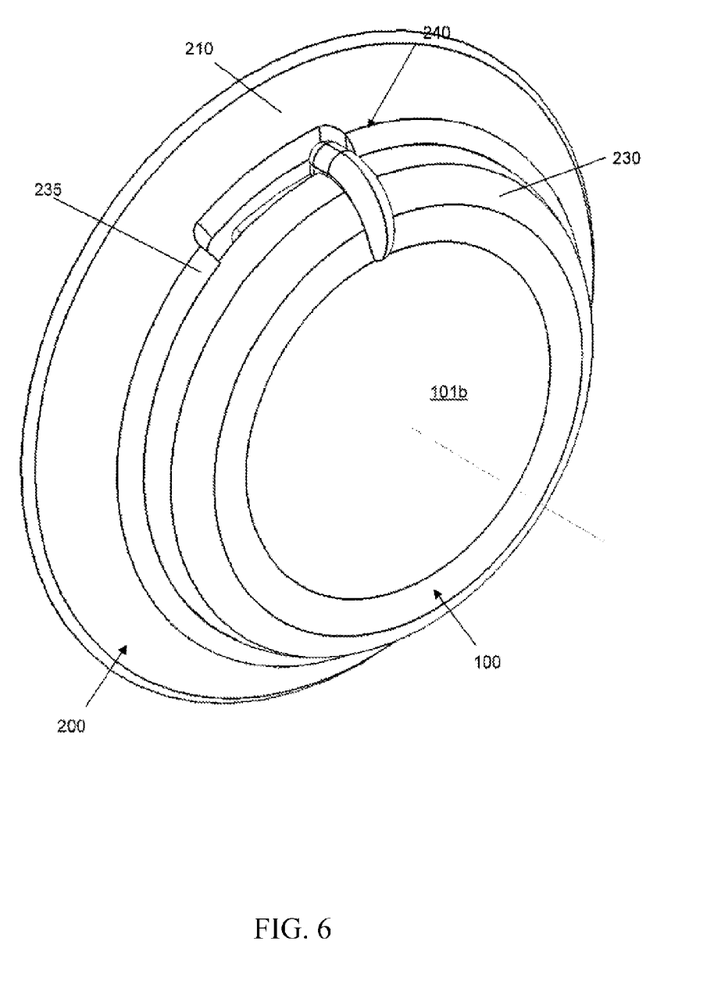
FIG. 6 illustrates a monitoring device and interface.
Figure 7:
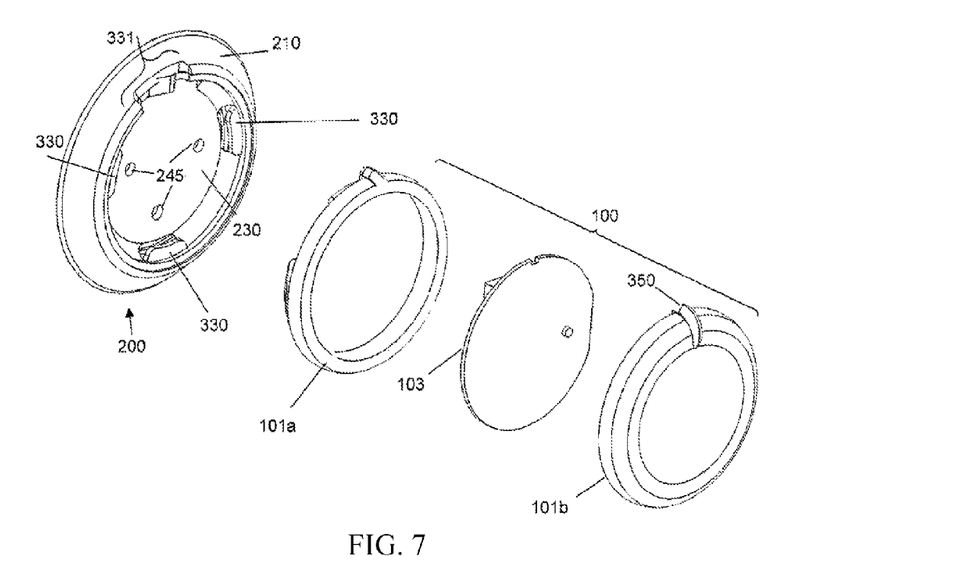
FIG. 7 illustrates a monitoring device and interface.
Figure 8:
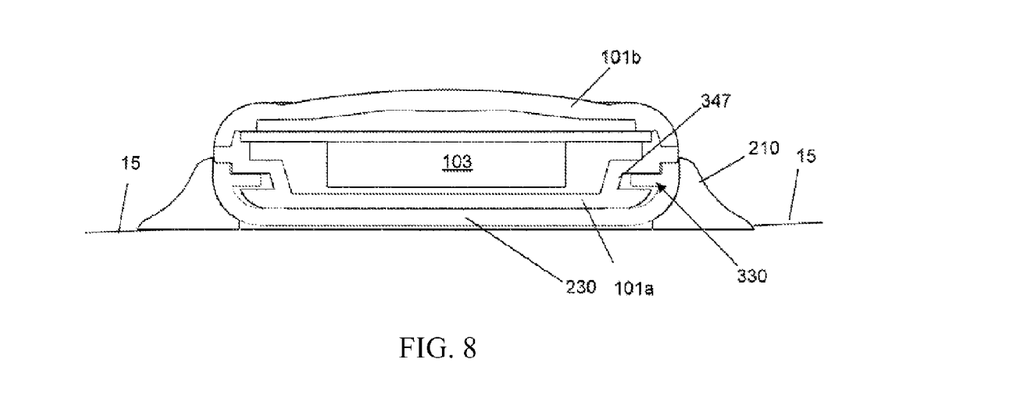
FIG. 8 illustrates a monitoring device and interface.
Figure 9:
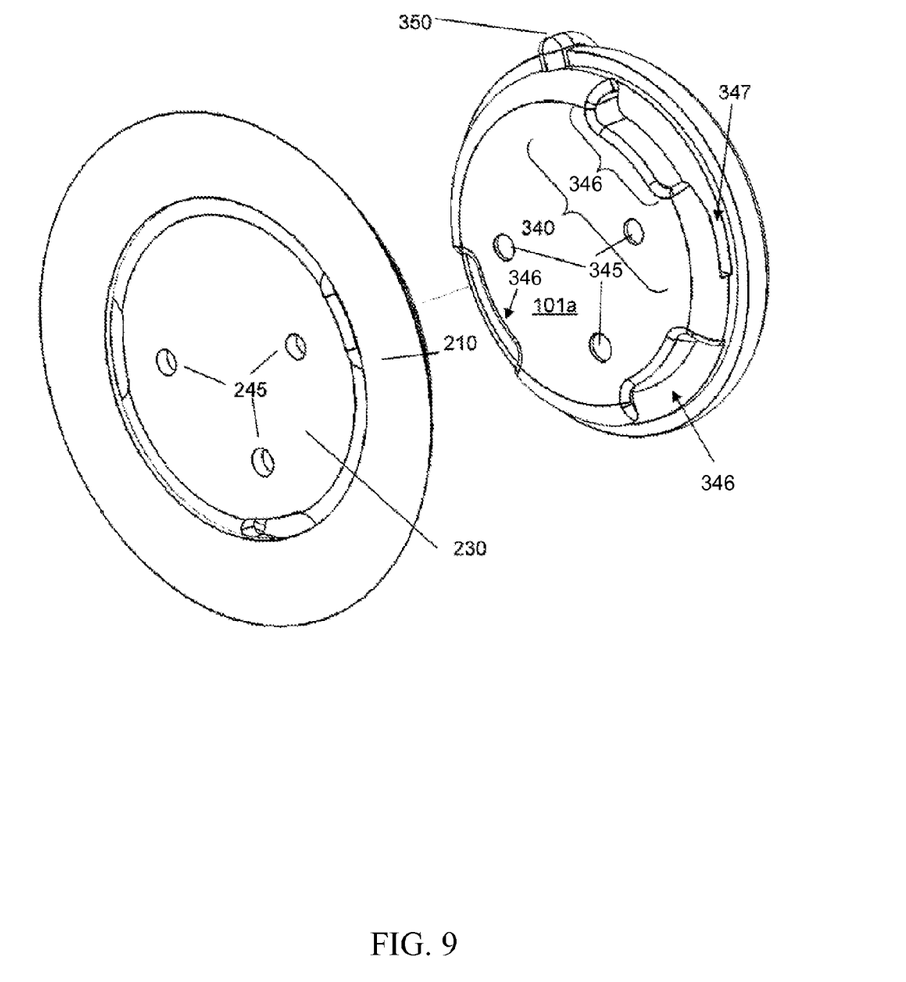
FIG. 9 illustrates a monitoring device and interface.
Figure 10:
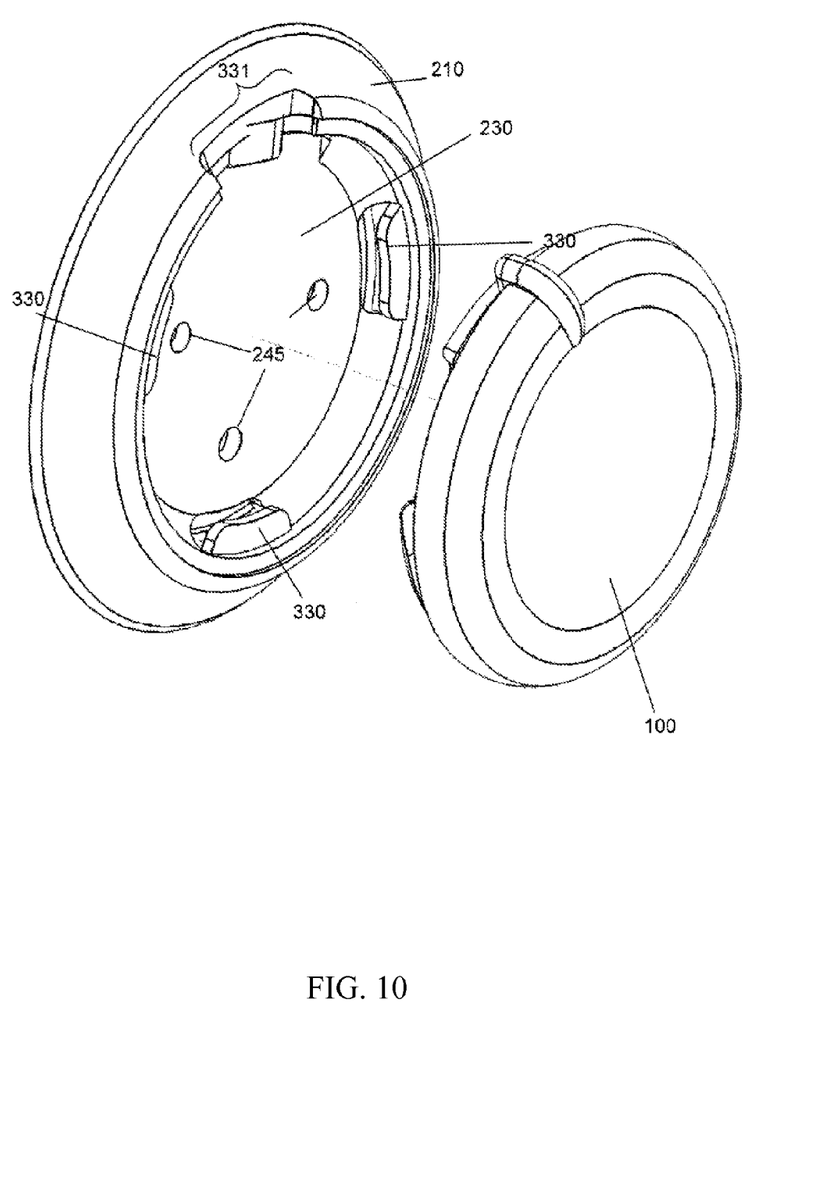
FIG. 10 illustrates a monitoring device and interface.
Figure 11:
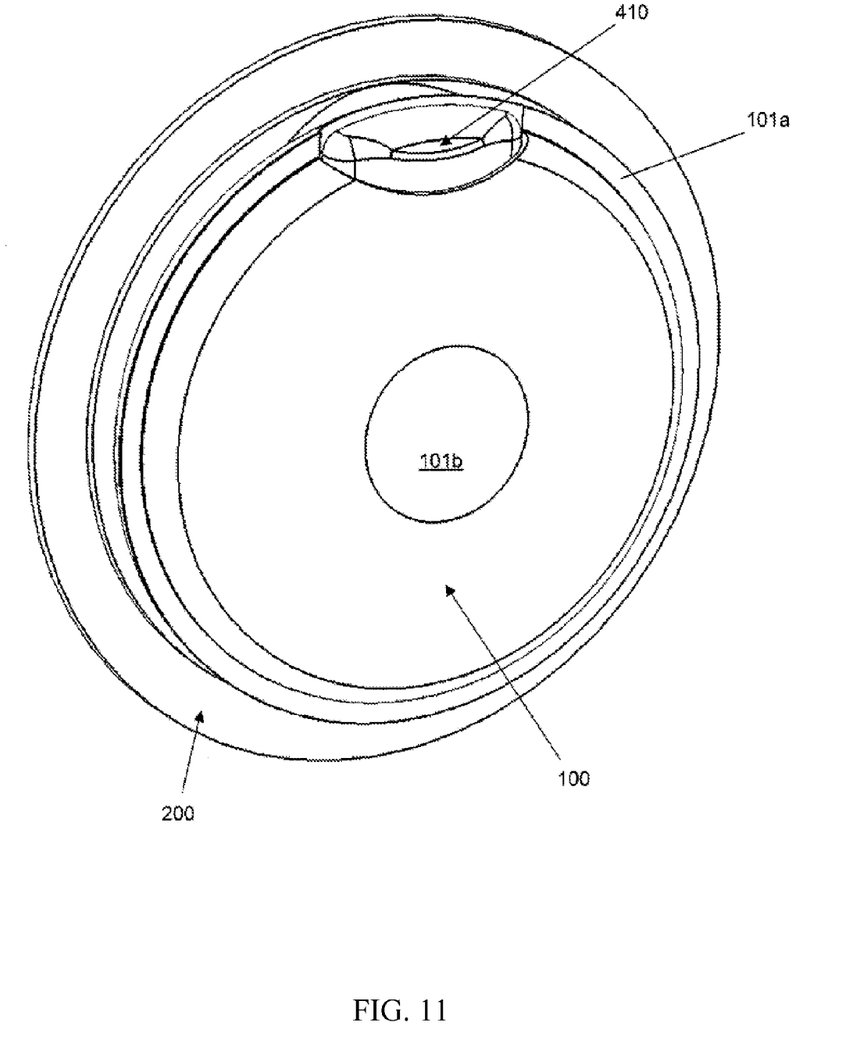
FIG. 11 illustrates a monitoring device and interface.
Figure 12:
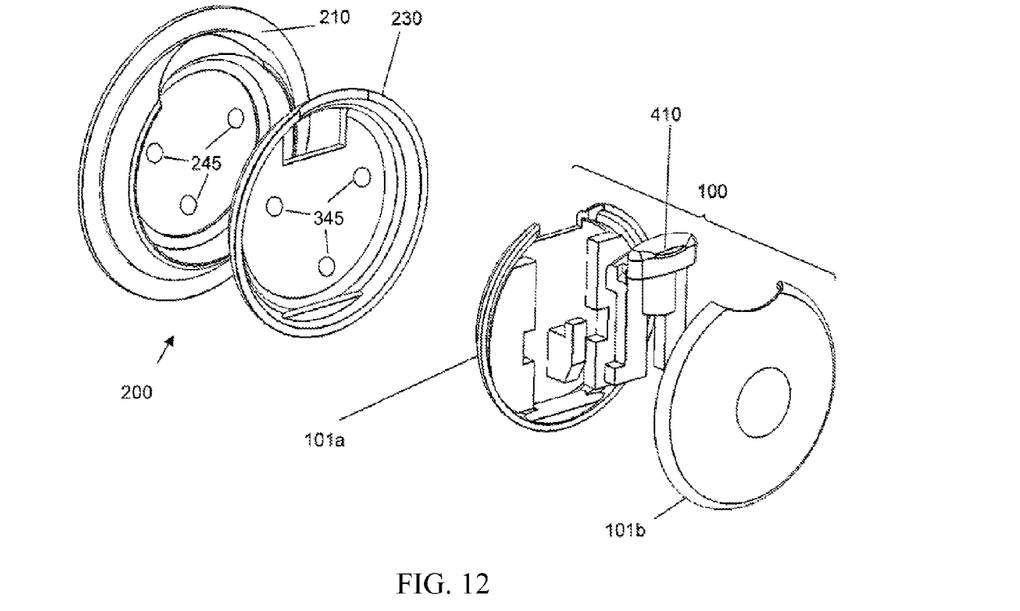
FIG. 12 illustrates a monitoring device and interface.

Referring to FIG. 4, the sides of the receptacle portion 230 are slightly concave and terminate in rim 235. The external lower rim edge 120 of the bottom portion 101a may have a diameter that is greater than (or that extends radially outward further than) the internal edge of the rim 235 of the receptacle portion 230. Thus, the receptacle portion 230 may be made of plastic or other deformable material that temporarily deforms outward to allow the external lower rim edge 120 to pass through the opening defined by the rim 235 of the receptacle portion 230 (or vice versa). Once in place, the internal edge of the rim 235 of the receptacle portion 230 pinches the external lower rim edge 120 to (1) prevent the monitoring device from being inadvertently dislodged; and (2) to urge the monitoring device 100 toward the receptacle portion. It is worth noting that the outside of the bottom portion 101 is slightly curved at 120 to more easily urge the rim 235 outward when pressure is applied by the user.

During use, the user would press the monitoring device 100 into the interface 200 until the external lower rim edge 120 of the bottom portion 101a passes through the opening defined by the rim 235 of the receptacle portion 230 and "snaps" into place. To remove the monitoring device 100, the user inserts a finger or thumb under the edge of the monitoring device 100 at the lip portion 240 (and as permitted due to the indentations 140 and 150) and pulls (or leverages) the monitoring device 100 out of the interface 200.

FIGS. 6-10 depict a monitoring device 100 and interface 200 according to a second example embodiment of the present invention. The monitoring device 100 comprises a bottom portion 101a and top portion 101b that mate together to house an internal portion 103 that comprises a processor, electronics, one or more transceivers, one or more light emitting LEDs (not shown (that are arranged to be visible through apertures (not shown) in the top portion 101b). The bottom portion 101a may include leaf springs 345 that conduct data from a plurality of sensors in or attached to the garment to the electronics (e.g., ADC, DSP, or processor) of the internal portion 103.

The interface 200 comprises a receptacle portion 230 that is fixedly attached to member 210. In this example, mounting member 210 comprises an elastomeric ring having an aperture therethrough. In addition, receptacle portion 230 includes three sensor pads 245 (which may comprise rivets that are riveted to the garment and provide a conductive path through the garment). Each sensor pad or rivet is electrically connected to one or more sensors attached to or integrated into the garment 15 such as via three respective conductors. In this example, one of the sensor pads connects to a sensor ground, one connects to an ECG sensor, and one sensor pad connects to a breathing rate sensor. Member 210 is fixedly attached to the garment 15 such as by heat bonding or sewn on, although other methods may be used. Thus, the sensor pads 245 may be connected to sensors in the garment via conductors that extend through the aperture 211 of the member 210 to other locations on the garment (outside the circumference of the ring).

In this embodiment, the receptacle portion 230 includes three inwardly protruding edges 330 and an opening 331 along the perimeter of the receptacle portion 230. In addition, the bottom portion 101a of the monitoring device 100 may include three edge engaging portions 340 that each include an opening 346 and a groove 347. The top portion 101b of the monitoring portion has a handle 350 to allow the user to urge the monitoring device 100 clockwise or counterclockwise. To removably attach the monitor 100 to the interface 200, the user inserts the monitor device 100 into the interface 200 so that the handle 350 enters into the opening 331 along the perimeter of the receptacle portion 230. When inserted so that the handle 350 enters into the opening 331 along the perimeter of the receptacle portion 230, the three protruding edges 330 of the receptacle portion 230 will be aligned with (in registration with) the three openings 346 of the monitoring device 100, to thereby allow the bottom portion 101a of the monitoring device 100 to abut the bottom center of the receptacle portion 230. The user may then rotate the monitoring device 100 approximately thirty degrees clockwise, which causes the three protruding edges 330 to slide into the three grooves 347 of the engaging portions 340. When fully rotated so that the protruding edges 330 are abutted against the end of the grooves 37, the leaf springs 345 of the monitoring device 100 will be in contact with the sensor pads 245 of the bottom receptacle portion 230. The grooves 347 may have a slightly narrowing opening so that the monitoring device 100 is held in place with a friction fit. In addition, the grooves 347 may be spaced away from the back surface of the bottom portion 101a so that, when the monitoring device 100 is fully inserted, the leaf springs 345 of the monitoring device 100 are urged toward the pads 245 (e.g., rivets) of the receptacle portion 230. Furthermore, the edge protrusions 330 may have an indentation (or vertical protrusion)—not shown— that engages a protrusion (or indentation) on the grooves 347 to keep the monitoring device 100 securely attached. The remaining aspects of this embodiment are substantially similar to the first embodiment.

FIGS. 11-14 depict a monitoring device 100 and interface 200 according to a third example embodiment of the present invention. The monitoring device 100 comprises a bottom portion 101a and a top portion 101b that mate together to house an internal portion that comprises a processor, electronics, one or more transceivers, one or more light emitting LEDs (not shown). The bottom portion 101a may include leaf springs 345 (or other sensor pads) that conduct data from a plurality of sensors in or attached to the garment to the electronics (e.g., DSP, ADC<processor) of the internal portion. The device 100 may include a user actuated member 410 which the user may actuate (e.g., press with a finger or thumb) that moves (e.g., toward the center of the device 100) to release the monitoring device 100 from the interface 200 to thereby allow removal.

Figure 13:
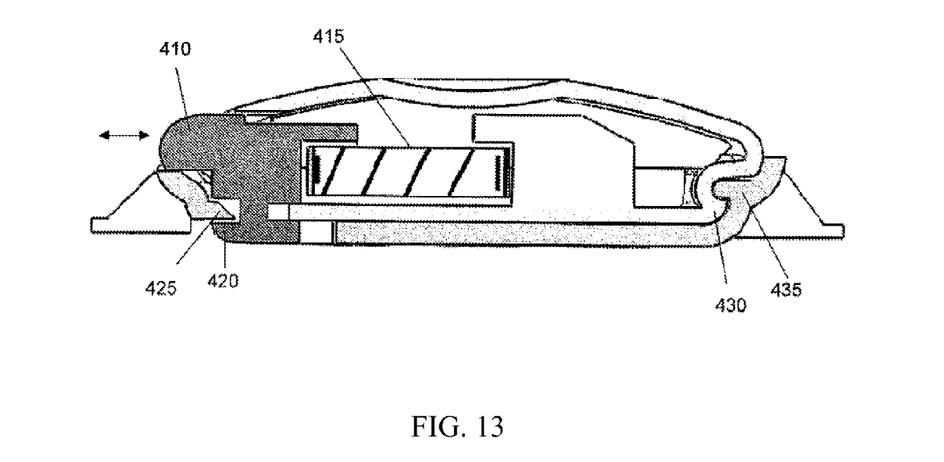
FIG. 13 illustrates a monitoring device and interface.
Figure 14:
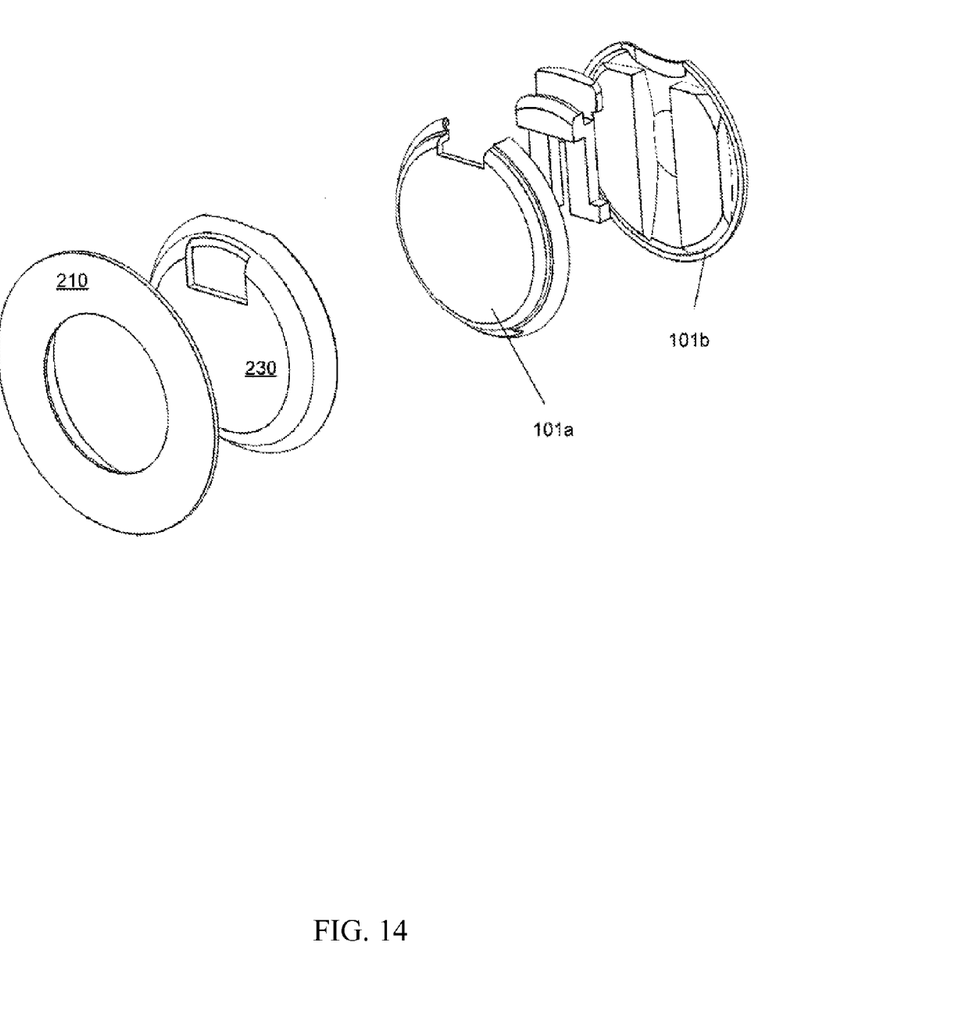
FIG. 14 illustrates a monitoring device and interface.

Referring to FIG. 13, the user actuated member 410 moves laterally when depressed as indicated by the arrow. The user actuated member 410 is adjacent to (or connected to) a spring 415 (or other urging member) that urges the user actuated member 410 outward. When the user presses the user actuated member 410 against the spring (or other urging member), a latching member 420 of the user actuated member 410 moves inward beyond a lip 425 of the interface 200 allowing removal of the monitoring device 100 from the interface 200. The opposite side of the monitoring device 100 includes a protrusion 430 that interfaces with a lip 435 to secure that side of the monitoring device 100 to the interface 200. The remaining aspects of this embodiment are substantially similar to the first embodiment.

Figure 15:
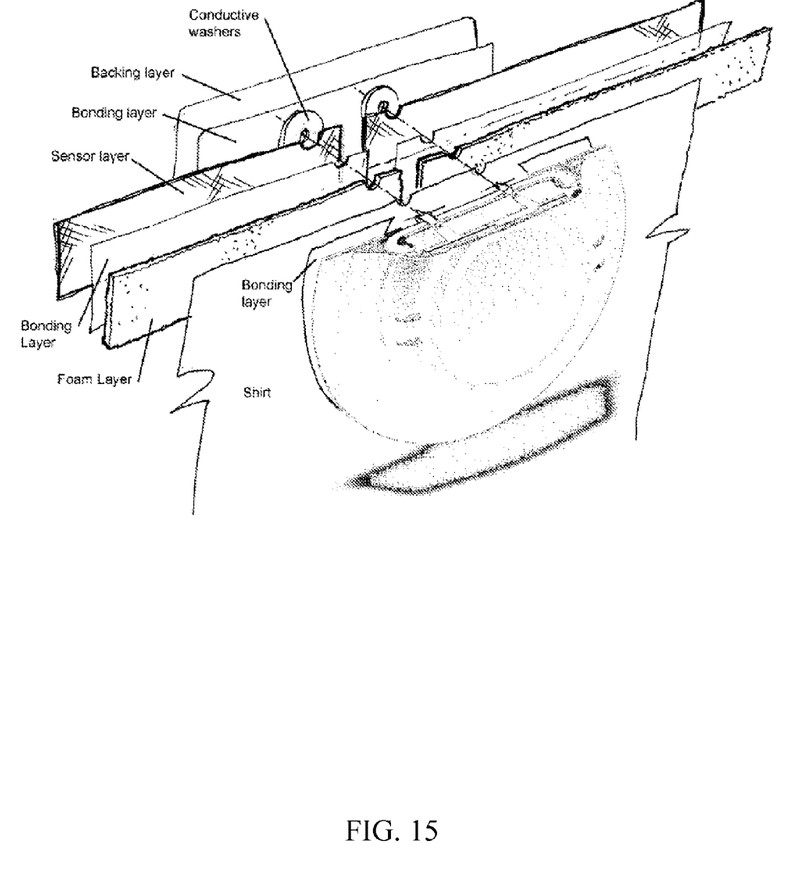

FIG. 15 illustrates an example embodiment of a monitoring device attached to a shirt in which the device/shirt assembly that includes the shirt, a first bonding layer, foam layer, a second bonding layer, a sensor layer (e.g., conductive fabric), a third bonding layer with conductive washers, and a backing layer.

In the above described embodiments, the receptacle (and monitoring device) may be formed from nylon or plastic. In addition, three conductive threads may be attached to the garment or woven therein to connect the three pads 245 of the receptacle to the sensors attached to or integrated into the garment. Alternately or additionally, plastic threads may be used to optically conduct the signals to and from the sensors.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

What is claimed is:

1. An apparatus, comprising:
an electronics portion;
a housing enclosing at least a portion of said electronics portion and comprising a plurality of housing sensor pads, each of the plurality of housing sensor pads comprising a leaf spring;
a garment, at least a portion of said garment having a plurality of stacked layers, one of said plurality of stacked layers being an electrically conductive sensor layer, said sensor layer
configured to measure at least a first physiological signal of a user wearing said garment;
an interface comprising a receptacle portion and a plurality of interface sensor pads, the interface configured to be fixedly attached to said garment in a chest area, each of the plurality of interface sensor pads comprising a protrusion;
said housing configured to be removably attached to said interface by snapping into the receptacle portion of the interface, wherein the plurality of protrusions are configured to orient the housing in an attached state with respect to the interface to ensure that each leaf spring of the plurality of housing sensor pads aligns with and contacts the protrusion of the plurality interface sensor pads when the housing is snapped into the interface,
the plurality of interface sensor pads including a first interface sensor pad coupled to a sensor ground, a second interface sensor pad coupled to an ECG sensor, and a third interface sensor pad coupled to a breathing rate sensor;
at least one of said interface sensor pads being electrically coupled to said sensor layer.

2. The apparatus of claim 1, wherein said housing includes a user actuated member having a first state in which said user actuated member engages said interface and a second state in which said user actuated member does not engage said interface and wherein said user actuated member is configured to transition from said first state to said second state by actuation of the user.

3. The apparatus of claim 1, wherein said interface is fixedly attached to said garment by any of heat bonding or sewing, or a combination thereof.

4. The apparatus of claim 1, wherein said electronics portion comprises:
a battery,
at least one wireless transceiver,
a processor,
at least one light emitting LED, and
an internal memory.

5. The apparatus of claim 4, wherein said at least one wireless transceiver comprises:
at least two wireless transceivers, each operable to communicate simultaneously with at least one remote device.

6. The apparatus of claim 1, wherein said apparatus is configured to measure at least one of heart rate, temperature, activity, ECG data, breathing rate, or posture.

* * * * *